United States Patent [19]

Moore

[11] Patent Number: Plant 5,460

[45] Date of Patent: May 7, 1985

[54] MINIATURE ROSE PLANT

[75] Inventor: Ralph S. Moore, Visalia, Calif.

[73] Assignee: Sequoia Nursery, Visalia, Calif.

[21] Appl. No.: 530,731

[22] Filed: Sep. 9, 1983

[51] Int. Cl.[3] ..... A01H 5/00

[52] U.S. Cl. ..... Plt./10

[58] Field of Search ..... Plt./10

*Primary Examiner*—Robert E. Bagwill

[57] ABSTRACT

The subject of the present disclosure is a new and distinct variety of miniature rose plant characterized by the unusual red color of the buds and flowers and by the profusion of bloom.

1 Drawing Figure

1

The present invention relates to a new and distinct variety of hardy, dwarf, bush type rose plant of the miniature class; the variety being primarily characterized—as to novelty—by orange red buds and flowers which in general color effect are similar to Sheri Anne (miniature—U.S. Plant Pat. No. 3,862).

The variety is further characterized by:

An abundance of bloom, with flowers, on mature plant, usually borne several to the stem in loose clusters or spray.

Little or no fragrance.

A plant which is vigorous, of somewhat spreading shape with semi-glossy to matt, small foliage with pointed leaflets; the buds and flowers being similar in form to Anytime (miniature—not patented) but smaller in size and with more petals.

The plant, which has a normal height of 12 inches or more and a spread up to 30 inches, can easily be maintained at lesser height or width by occasional trimming.

A plant which grows and blooms satisfactorily both in greenhouse and outdoors; is good for growing in pots or hanging baskets; and provides excellent garden decoration as well as cut flowers.

The present variety of miniature rose was originated by me at Sequoia Nursery located at Visalia, Calif., under conditions of careful control and observation as a cross between Little Chief (miniature—not patented) as the seed parent and Anytime (miniature—not patented), as the pollen parent.

Subsequent to origination of the variety I successfully reproduced it, at Sequoia Nursery located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy: dwarf; bushy; spreading; seedling; greenhouse; outdoors; cut flowers; garden decoration; potted plant.

Class: Miniature.

*International identification.*—Variety: MORanium. Commercial synonym: AUTUMN FIRE.

Flowers borne: Usually several together in clusters of 3–15 or more on slender wirey stems.

2

Quantity of bloom: Abundant both outside and in greenhouse.

Bud:

*Peduncle.*—Medium to long; slender but sturdy; erect; medium green, sometimes tinted bronze (outdoors);

*Hairs.*—Very short (more like fuzz).

*Before calyx breaks.*—Size — small. Form long; pointed with several foliaceous apendages and few very small, very fine, hairs on surface of bud; with foliaceous parts extending beyond the tip of the bud equal to one-half or less of its length. NOTE: The fine hairs on peduncle and bud can only be seen with the aid of a reading glass. Color — medium green, occasionally tinted with bronze (outdoors).

*As calyx breaks.*—Color — red. Opening: opens well in all weather.

Bloom:

*Size when fully open.*—Small, averaging about 30 mm ($1\frac{1}{4}''$).

*Petalage.*—Semi-double — averaging about 15 petals, arranged regularly plus sometimes several small petaloids.

*Form.*—Cupped at first, becoming more flat and open, with petals reflexing loosely outward. Open flowers show stamens.

Petals: Fairly thick; satiny on inside and on outside surfaces.

*Shape.*—Outside petals, broad lanceolate to wedge shaped with rounded tip; intermediate — broad lanceolate to wedge shape with rounded tip; inside — similar to intermediate petal but narrower.

Color (newly opened flower from a plant grown in plastic greenhouse (September 1983), Visalia, Calif.:

*Outside petal.*—Outside surface — near Geranium Lake 20/1 with blackish veining (or tint) with small blueish white area at base. Inside surface — near Scarlet 19/1 with blackish veining (or shading) and with a lavender or blueish area at base. The red color can vary from Scarlet 19/1 (or similar) to Vermillion 18/1 (or similar) — or lighter. The unusual shade or shades of red of this flower vary and so are difficult to describe in precise terms.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — bright orange red resembling a geranium. Three days open — color similar to newly opened flowers. Behavior — opens well in all weather. Color lasts better than most of similar coloring. Spent petals drop off. Flower longevity (June 1983) — plant in pot 7–14 days or longer. Cut flowers at living room temperature. 4–7 days.

Reproductive organs:

*Stamens.*—Abundant, arranged regularly about pistils.

*Filaments.*—Varying length, medium to short length, yellow.

*Anthers.*—Well formed; yellow.

*Pollen.*—Moderate amount.

*Pistils.*—Average number.

*Styles.*—Fairly even; medium to short length; bunched; color — whitish to pale yellow.

*Ovaries.*—All enclosed in calyx.

*Hips.*—None to few.

*Sepals.*—Permanent; spear shaped; recurved against peduncle.

*Seed.*—Few or none.

Foliage:

*Leaves.*—Compound of five (sometimes three or seven) leaflets; fairly small; leathery; semi-glossy to matt.

*Leaflets.*—Shape: broad lanceolate; nearly oval; apex acute; base rounded or rounded acute. Margin serrate. Color: medium to dark green; new growth — normal (medium) green. Rachis: medium strength; upperside may have a few tiny short prickles or hairs, grooved; underside sparsely thorny with few or no tiny prickles.

Stipules: medium long to long; narrow to medium width; short length, narrow points which turn out usually at about 45 degrees.

Growth:

*Habit.*—Dwarf; bushy; spreading; much branched.

*Growth.*—Free vigorous; internodes short.

*Canes.*—Medium slender; sturdy.

*Main stems.*—Color: medium green.

*Thorns.*—Average; slender, nearly straight, inclined slightly downward; color; brown. Prickles — none.

*Branches.*—Color; medium green. Thorns: moderate number; medium length; slender; inclined downward.

*Medium oval base.*—Prickles: none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, spreading, much branched habit, substantially as illustrated and described, characterized by buds and flowers of a generally orange red color, being of a shade generally near Scarlet 19/1 or lighter, the bud and flower resembling the variety Anytime (not patented) in form with more petals, and slightly smaller size; and further characterized by a plant of vigorous and compact growth habit, easy to propagate from cuttings or by budding, with an abundance of small to medium size semi-glossy to matt foliage and an abundance of flowers borne usually in loose clusters (or spray) of 3 to 15 or more.

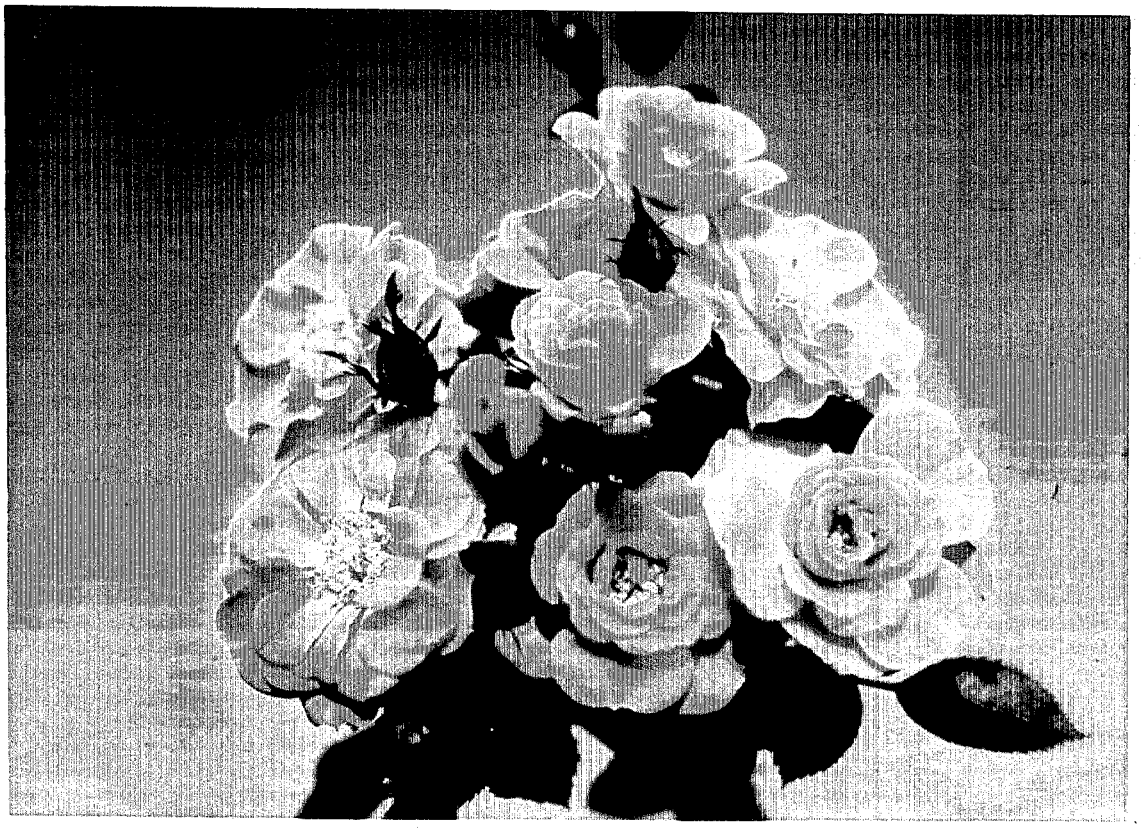

* * * * *